(12) United States Patent
Lathrop

(10) Patent No.: US 10,478,207 B2
(45) Date of Patent: Nov. 19, 2019

(54) SURGICAL GRASPER

(71) Applicant: Vanderbilt University, Nashville, TN (US)

(72) Inventor: Ray A. Lathrop, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 284 days.

(21) Appl. No.: 15/129,893

(22) PCT Filed: Apr. 30, 2015

(86) PCT No.: PCT/US2015/028581
§ 371 (c)(1),
(2) Date: Sep. 28, 2016

(87) PCT Pub. No.: WO2015/168441
PCT Pub. Date: Nov. 5, 2015

(65) Prior Publication Data
US 2017/0172595 A1   Jun. 22, 2017

Related U.S. Application Data

(60) Provisional application No. 61/986,390, filed on Apr. 30, 2014.

(51) Int. Cl.
A61B 17/29    (2006.01)
A61B 17/062   (2006.01)
A61B 34/00    (2016.01)

(52) U.S. Cl.
CPC ........ A61B 17/2909 (2013.01); A61B 17/062 (2013.01); A61B 17/29 (2013.01);
(Continued)

(58) Field of Classification Search
CPC ................ A61B 17/29; A61B 17/2909; A61B 2017/291; A61B 2017/2923;
(Continued)

(56) References Cited

U.S. PATENT DOCUMENTS

| 5,209,747 A | 5/1993 | Knoepfler |
| 5,704,925 A | 1/1998 | Otten et al. |

(Continued)

FOREIGN PATENT DOCUMENTS

| WO | 03/001986   | 1/2003 |
| WO | 2010019001  | 2/2010 |

(Continued)

OTHER PUBLICATIONS

PCT/US2015/028581 International Search Report and Written Opinion of the International Searching Authority dated Sep. 24, 2015 (9 pages).

(Continued)

*Primary Examiner* — Ashley L Fishback
(74) *Attorney, Agent, or Firm* — Michael Best & Friedrich LLP

(57) ABSTRACT

A surgical grasper includes a first handle arm, a second handle arm pivotally coupled to the first handle arm, a tool body pivotally coupled to both the first handle arm and the second handle arm, a first jaw member pivotally coupled to the tool body, a second jaw member pivotally coupled to the tool body, a first tension element coupled to both the first handle arm and to the first jaw member, a second tension element coupled to both the second handle arm and to the second jaw member, and a lock that locks relative movement between the first and second handle arms. Rotational movement of the first and second handle arms generates correlated rotational movement of the first and second jaw members.

20 Claims, 14 Drawing Sheets

(52) U.S. Cl.
CPC ........ *A61B 34/71* (2016.02); *A61B 2017/291* (2013.01); *A61B 2017/2919* (2013.01); *A61B 2017/2927* (2013.01); *A61B 2017/2946* (2013.01)

(58) Field of Classification Search
CPC .... A61B 2017/2919; A61B 2017/2927; A61B 2017/2946
See application file for complete search history.

(56) References Cited

U.S. PATENT DOCUMENTS

| | | | |
|---|---|---|---|
| 5,853,412 | A | 12/1998 | Mayenberger |
| 5,922,007 | A * | 7/1999 | Hoogeboom ...... A61B 17/2909 606/205 |
| 2006/0069407 | A1 | 3/2006 | Weber |
| 2006/0206144 | A1 * | 9/2006 | Miersch ............ A61B 17/062 606/205 |
| 2008/0306342 | A1 * | 12/2008 | Leonard ............. A61B 17/2909 600/131 |
| 2010/0011900 | A1 | 1/2010 | Burbank |
| 2010/0063538 | A1 | 3/2010 | Spivey et al. |
| 2012/0220831 | A1 | 8/2012 | Cooper et al. |

FOREIGN PATENT DOCUMENTS

| | | |
|---|---|---|
| WO | 2013082220 | 6/2013 |
| WO | 2013/158974 | 10/2013 |

OTHER PUBLICATIONS

PCT/US2015/028581 International Preliminary Report on Patentability dated Nov. 1, 2016 (1 pages).
European Patent Office Search Report for Application No. 15785341.7 dated Dec. 5, 2017, 7 pages.

* cited by examiner

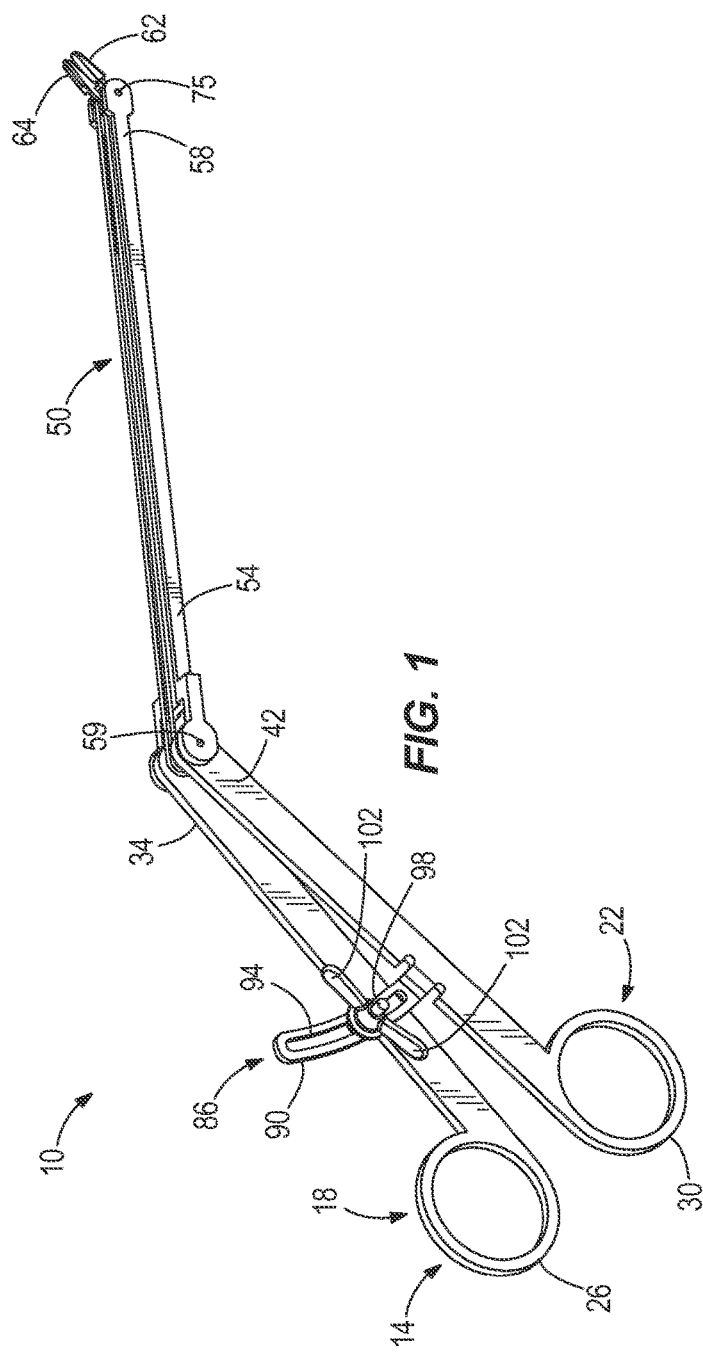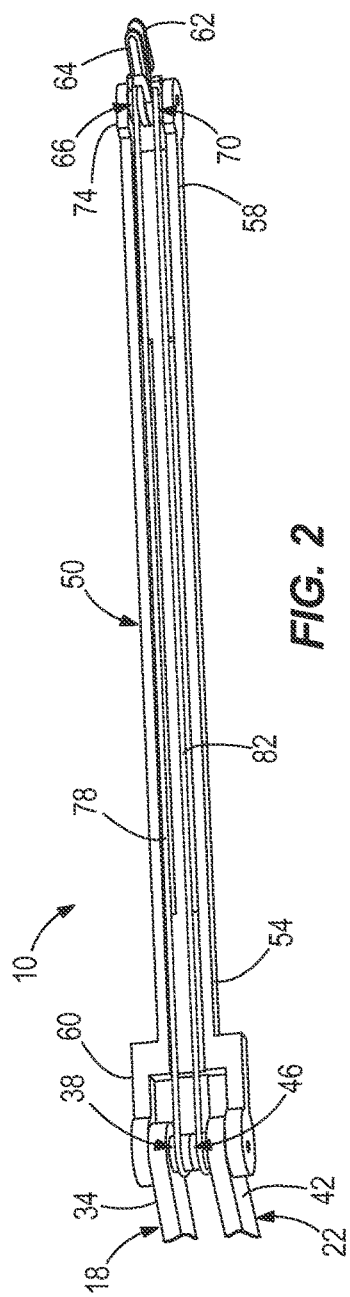

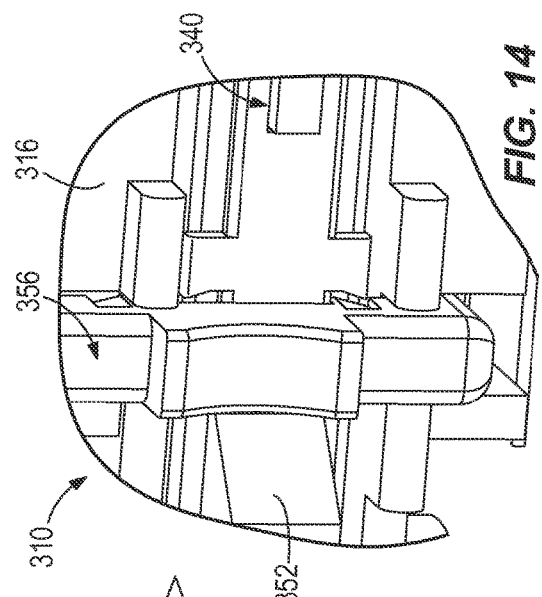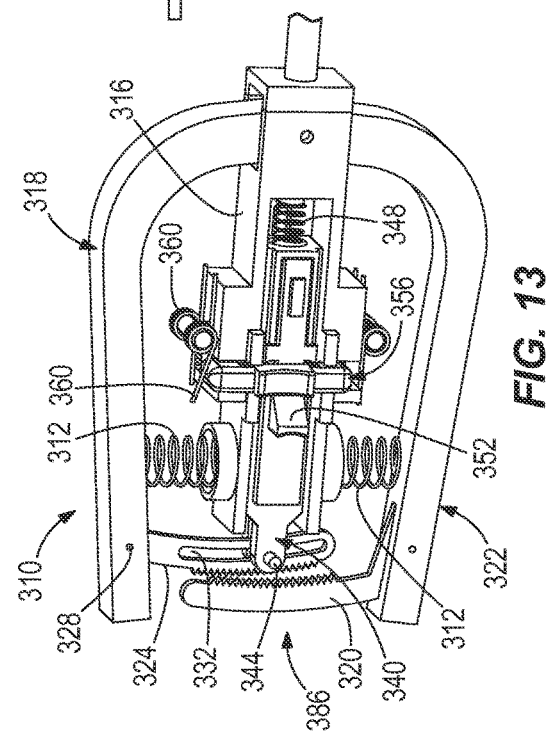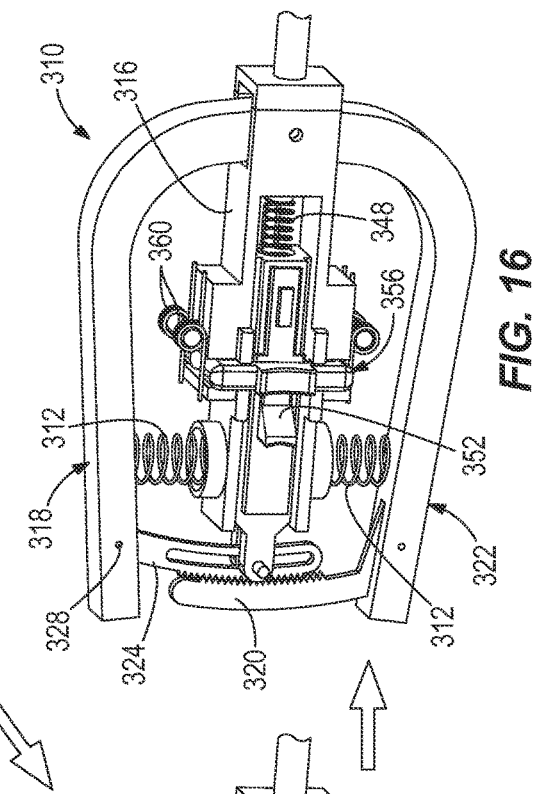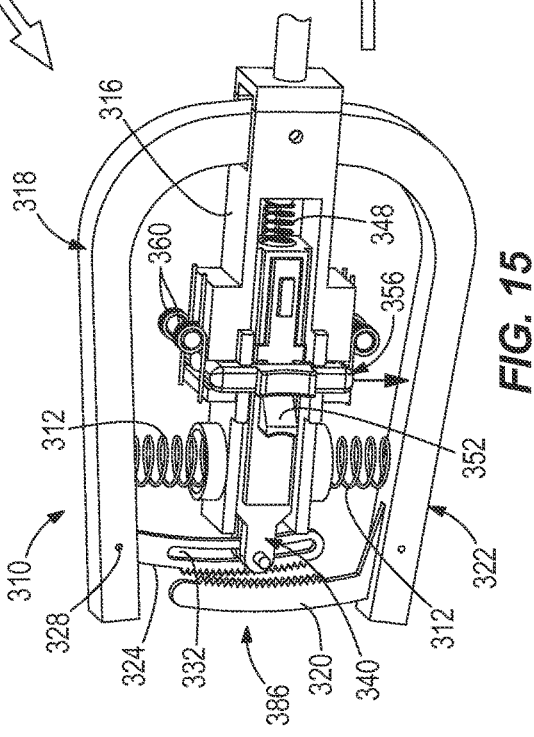

SURGICAL GRASPER

CROSS-REFERENCE TO RELATED APPLICATIONS

This application is a non-provisional of and claims priority to U.S. Provisional Application No. 61/986,390, filed Apr. 30, 2014, the entire contents of which are incorporated herein by reference.

FIELD OF THE INVENTION

The present invention relates generally to graspers, and in particular to a lock for a laparoscopic surgical grasper.

BACKGROUND OF THE INVENTION

Surgical graspers are commonly used by a surgeon to grasp onto skin, tissue or other anatomy or structures (e.g., surgical needles and other tools such as amiable surgical lasers) during a medical procedure. The graspers include a pair of opposed jaws that are opened and closed relative to one another with a pair of handles to pinch, or grasp, onto the structure. Traditional manual deflectable/dexterous surgical graspers use separate tension elements to close the jaw members and to change the angle or direction of grasping. The separate tension elements do not affect one another, and are independent. In some graspers, the jaw members are locked by applying tension to one of the tension elements and then anchoring the tension element so that the tension element cannot move relative to a tool body or main shaft.

SUMMARY OF THE INVENTION

In accordance with one construction of the invention, a surgical grasper includes a first handle arm, a second handle arm pivotally coupled to the first handle arm, a tool body pivotally coupled to both the first handle arm and the second handle arm, a first jaw member pivotally coupled to the tool body, a second jaw member pivotally coupled to the tool body, a first tension element coupled to both the first handle arm and to the first jaw member, a second tension element coupled to both the second handle arm and to the second jaw member, and a lock that locks relative movement between the first and second handle arms. Rotational movement of the first and second handle arms generates correlated rotational movement of the first and second jaw members.

In accordance with another construction of the invention, a surgical grasper includes a first handle arm, a second handle arm pivotally coupled to the first handle arm, and a lock that locks relative movement between the first and second handle arms. The lock includes a first ratchet arm fixed to the first handle arm, a second ratchet arm pivotally coupled to the second handle arm, a pusher element coupled to the second ratchet arm that moves the second ratchet arm toward and away from the first ratchet arm, and a lockout element releasably coupled to the pusher element that locks a position of the pusher element.

Other aspects of the invention will become apparent by consideration of the detailed description and accompanying drawings.

BRIEF DESCRIPTION OF THE DRAWINGS

FIG. 1 is a perspective view of a grasper according to one construction of the invention.

FIG. 2 is a perspective view of a tool body portion of the grasper of FIG. 1.

FIGS. 13 and 14 are perspective views of a portion of the grasper of FIG. 7, with the pusher element pressed back farther.

FIG. 15 is a perspective view of a portion of the grasper of FIG. 7, with the lockout element returning back to a centered position.

FIG. 16 is a perspective view of a portion of the grasper of FIG. 7, with the pusher element returning back to the position illustrated in FIG. 7.

Figure 3:
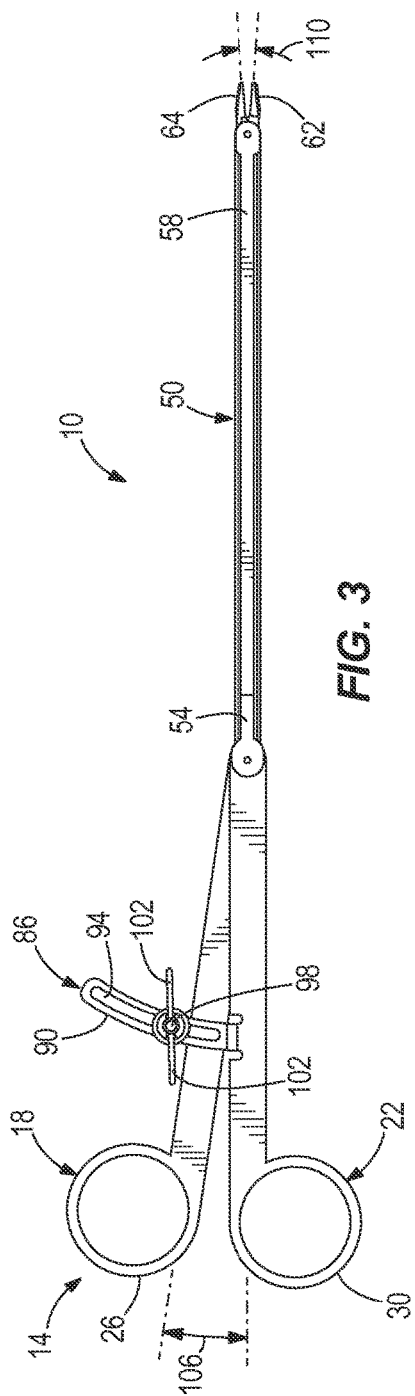
FIG. 3 is a side view of the grasper of FIG. 1 in a first operating position.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limited.

DETAILED DESCRIPTION

FIGS. 1-6 illustrate a surgical tool, such as a surgical grasper 10. While the grasper 10 is illustrated and described in the context of a surgical laparoscopic grasper, the grasper 10 may be used outside of the surgical field, and in some constructions outside of the medical field, to grasp and hold an object or objects.

With reference to FIG. 1, the grasper 10 includes a handle 14 having a first handle arm 18 and a second handle arm 22 that are pivotally coupled to one another. The first handle arm 18 includes a first grip portion 26, and the second handle arm 22 includes a second grip portion 30. The illustrated grip portions 26, 30 are loops through which a surgeon inserts one or more fingers to grip and move the handle arms 18, 22. In other constructions, the grip portions 26, 30 have other suitable structures that facilitate gripping and movement of the handle arms 18, 22.

With reference to FIGS. 1 and 2, the first handle arm 18 includes a first pivot end 34 disposed opposite the first grip portion 26. The first pivot end 34 includes a first pulley 38 (FIG. 2). The second handle arm 22 includes a second pivot end 42 disposed opposite the second grip portion 30. The second pivot end 42 includes a second pulley 46 (FIG. 2).

With reference to FIGS. 1-4, the grasper 10 includes a tool body 50 pivotally coupled to the handle 14 and, more specifically to each of the first and second handle arms 18, 22. The illustrated tool body 50 is an elongated structure having a first end 54 and a second end 58. As illustrated in FIGS. 1 and 2, the first end 54 is pivotally coupled to the first and second pulleys 38, 46 with a pin 59 (FIG. 1) extending through the first and second pulleys 38, 46 (e.g., through open centers of the first and second pulleys 38, 46). The first end 54 includes a receiving portion 60 (U-shaped in the illustrated embodiment) that receives the first and second pivot ends 34, 42 and the first and second pulleys 38, 46. Other constructions include different structures for the first end 54, including having T-shaped portions instead of U-shaped portions (e.g., where the arms 18, 22 are coupled to the outside ends of the "T" and a pivot axis for the tool body is at the top of the "T"), or other types of shapes for the receiving portion 60.

With continued reference to FIGS. 1-4, the grasper 10 further includes a first jaw 62 and a second jaw 64 pivotally coupled both to one another and to the second end 58 of the tool body 50. The first and second jaws 62, 64 are used to grasp skin, tissue, or other anatomy or structures during a medical procedure (e.g., during a laparoscopic procedure). As illustrated in FIG. 2, the first jaw 62 includes a first pulley 66, and the second jaw includes a second pulley 70. The second end 58 of the tool body 50 includes a U-shaped portion 74 that receives and is pivotally coupled to the first and second pulleys 66, 70 with a pin 75 (FIG. 1) extending through the first and second pulleys 66, 70 (e.g., through open centers of the first and second pulleys 66, 70).

With continued reference to FIGS. 1 and 2, the grasper 10 includes a first tension element 78 (e.g., wire, cable, etc.) that extends around the first pulleys 38, 66, and a second tension element 82 (e.g., wire, cable, etc.) that extends around the second pulleys 46, 70. The tension element 78 couples movement of the first handle arm 18 and the first pulley 38 to movement of the first jaw 62, and the tension element 82 couples movement of the second handle arm 22 and the second pulley 46 to the second jaw 64.

When the first handle arm 18 and the second handle arm 22 are spread apart (e.g., by the surgeon grasping the grip portions 26, 30 and spreading the grip portions 26, 30 apart), the first and second jaws 62, 64 are similarly caused to spread apart, due to the movement of the tension elements 78, 82 along the pulleys 38, 46, 66, 70. When the first handle arm 18 and the second handle arm 22 are pressed together (e.g., by the surgeon grasping the grip portions 26, 30 and pressing the grip portions 26, 30 together), the first and second jaws 62, 64 are similarly caused to press together, or pinch, due to the movement of the tension elements 78, 82 along the pulleys 38, 46, 66, 70.

Figure 4:
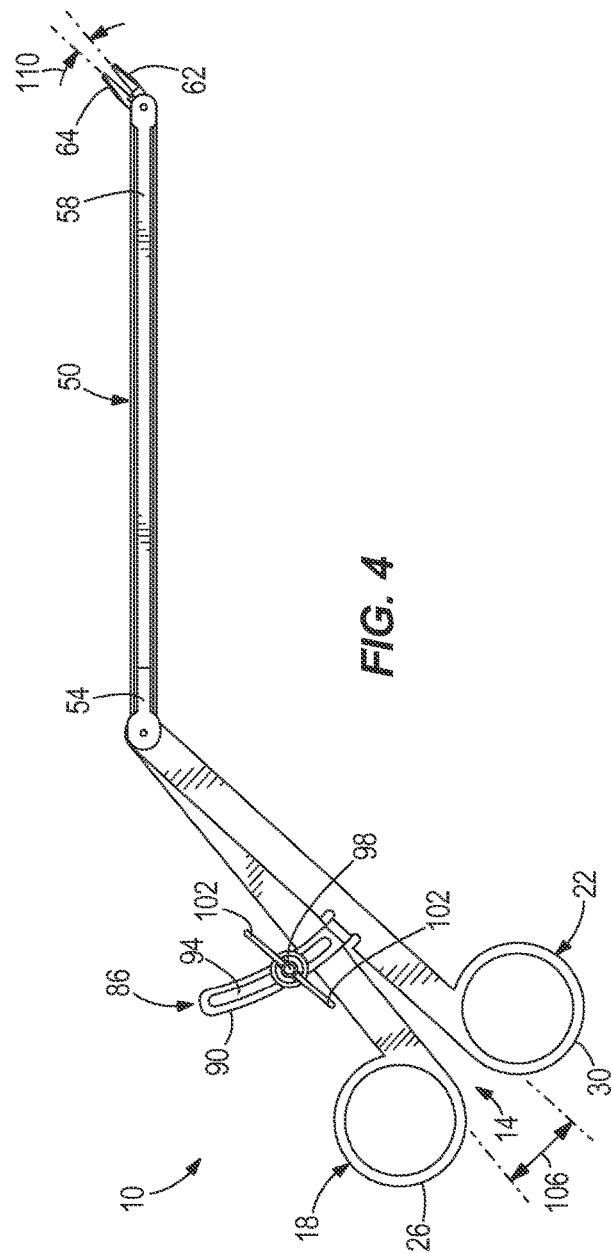
FIG. 4 is a side view of the grasper of FIG. 1 in a second operating position.

With reference to FIGS. 1, 3, and 4, the grasper 10 also includes a lock 86 that locks relative movement of the first and second handle arms 18, 22. The illustrated lock 86 is a sliding friction lock that includes an elongate protrusion 90 extending from the second handle arm 22. The protrusion 90 includes a slot 94 (e.g., an elongate slot). A fastener 98 is extended partially through the slot 94 to lock onto the protrusion 90 by twisting wings 102 of the fastener 98. The fastener 98 prevents (e.g., blocks) the first and second handle arms 18, 22 from spreading apart from one another past a predefined angle 106 (FIGS. 3 and 4). The fastener 98 is adjustable, such that the angle 106 is also adjustable as desired.

As illustrated in FIGS. 3 and 4, with the first and second handle arms 18, 22 spread apart by the angle 106, the first and second jaws 62, 64 are also spread apart by a predefined angle 110. With the fastener 98 locked onto the protrusion 90, the first and second handle arms 18, 22 are able to pivot and rotate together in a parallel manner about the first end 54, and in particular about the pulleys 38, 46 of the tool body 50. As the first and second handle arms 18, 22 pivot together, both the angle 106 between the first and second arms 18, 22 and the angle 110 between the first and second jaws 62, 64 remain constant.

As illustrated in FIGS. 3 and 4, locking the relative movement of the handle arms 18, 22 and the jaws 62, 64 allows the jaws 62, 64 to be deflected and the angle or direction of grasping (as seen between FIGS. 3 and 4) to change while the jaws 62, 64 are still locked relative to one another. This eliminates the requirement of having separate mechanisms to both open and close the jaws and to change a grasping angle or direction.

Figure 4A:
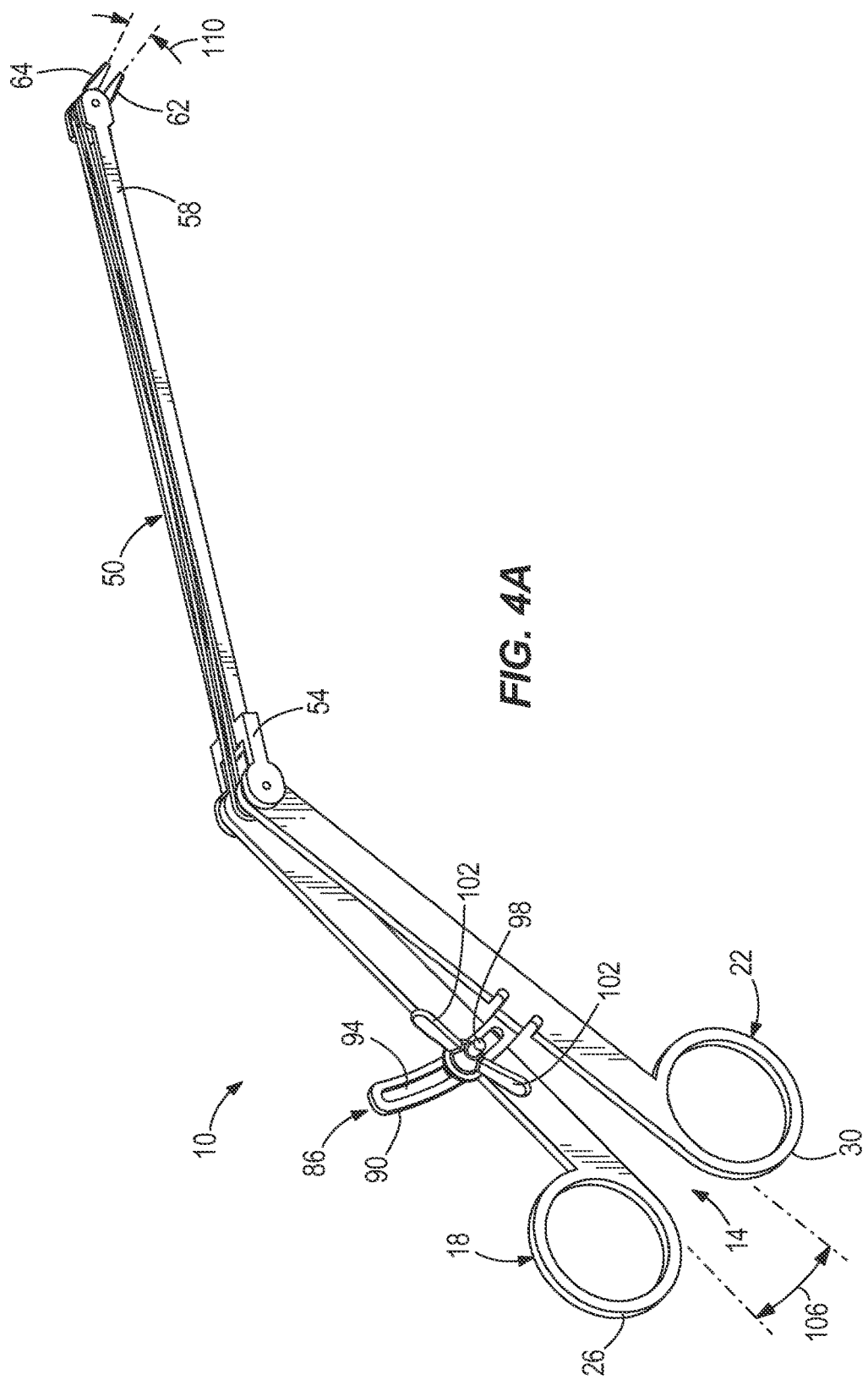
FIG. 4A is a side view of the grasper of FIG. 1, but with jaw members that rotate in an opposite correlated manner to rotational movement of handle arms.

With reference to FIG. 4A, in some constructions rotational movement of the handle arms 18, 22 in one direction results in a corresponding rotational movement of the jaws 62, 64 in an opposite direction (e.g., clockwise movement of the handle arms 18, 22 resulting in counterclockwise movement of the jaws 62, 64). For example, in some constructions the tension elements 78, 82 are reversed and routed in a figure eight configuration to generate opposite movement of the jaws 62, 64 relative to the handle arms 18, 22.

In some constructions movement of the handle arms 18, 22 by a first angle results in movement of the jaws 62, 64 by a second, different angle. For example, in some constructions rotational movement of the handle arms 18, 22 by twenty degrees in a clockwise or counterclockwise direction results in the jaws 62, 64 rotating by fifteen degrees, thirty degrees, or another angle in a clockwise or counterclockwise direction. Various other angles and ranges of ranges are also possible. In some constructions the ratio of sizes of the pulleys 38, 46, 66, 70 and/or the arrangement of the tension elements 78, 82 are adjusted to determine the first and second angles.

Figure 5:
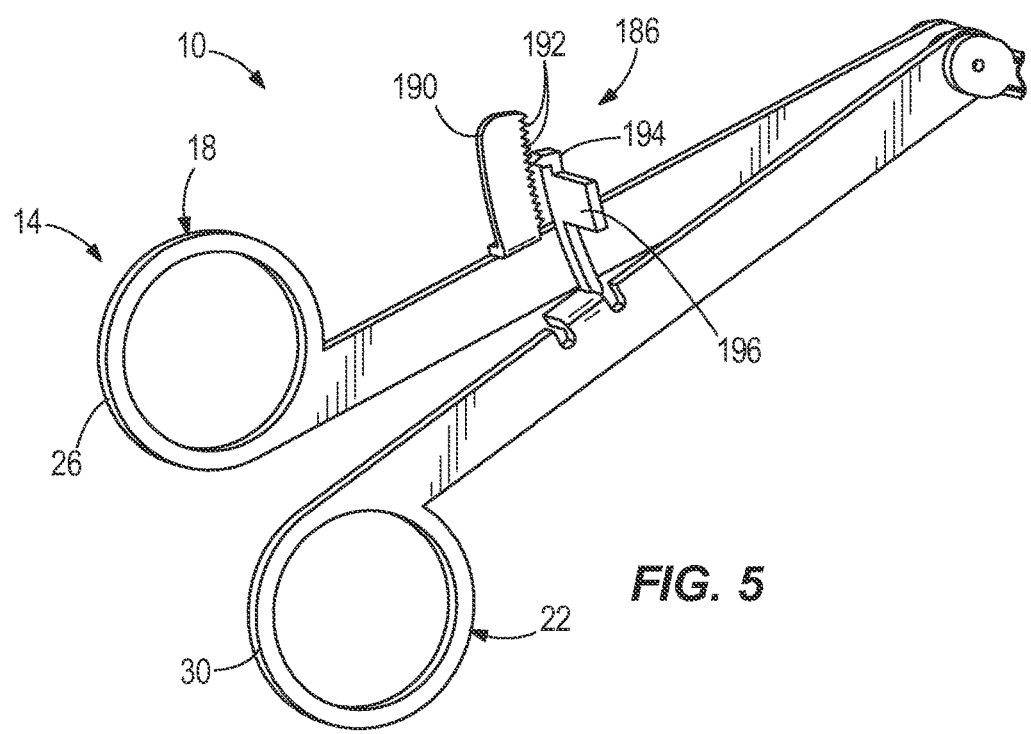
FIGS. 5 and 6 are perspective views of alternative locking mechanisms for the grasper of FIG. 1.
Figure 6:
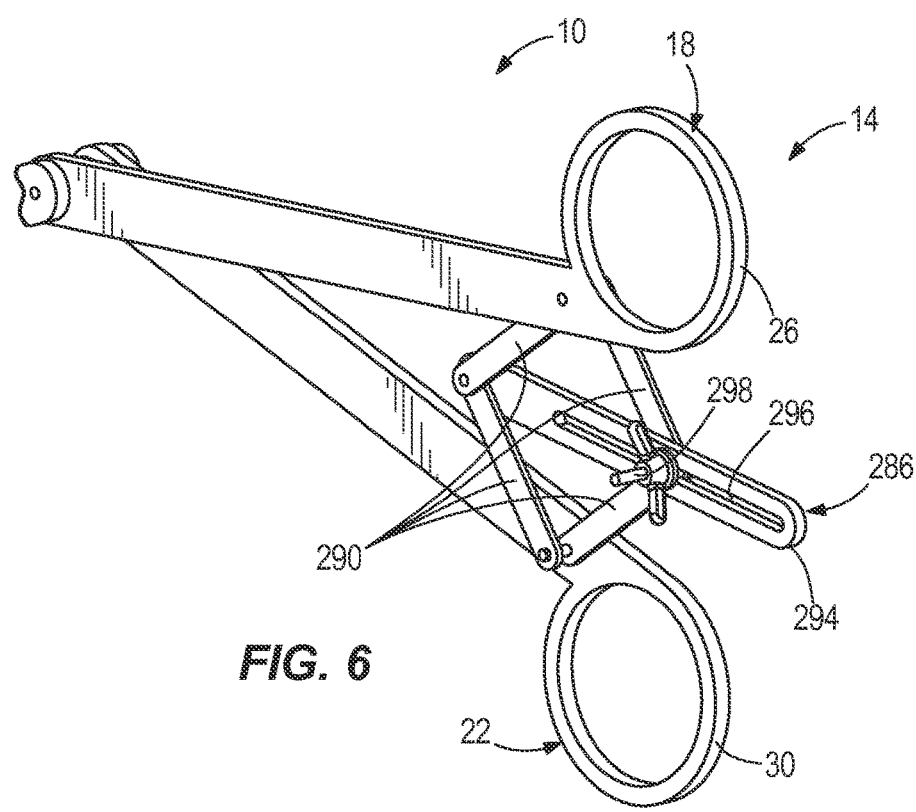

FIGS. 5 and 6 illustrate other locking mechanisms to lock the handle arms 18, 22 of the grasper 10 described above. For example, with reference to FIG. 5, in some constructions, the grasper 10 includes a lock 186 that is a ratcheting-type locking mechanism. The illustrated lock 186 includes a projection 190 extending from the first handle arm 18 that includes teeth 192. A spring-biased member 194 extending from the second handle arm 22 engages the teeth 192, and includes a tab 196 that is pressed to release the engagement of the spring-biased member 194 with the teeth 192.

With reference to FIG. 6, in some constructions the grasper 10 includes a lock 286 that uses a friction lock with arms 290 that pivot relative to one another in a scissors-like manner to spread or close handle arms 18, 22, and an intermediate member 294 that includes a slot 296 that receives a fastener 298, similar to fastener 98. By tightening the fasteners 298 onto the intermediate member 294, movement of the arms 290 is locked, thereby locking movement of the handle arms 18, 22 relative to one another.

Other constructions of the surgical grasper 10 can include different types of suitable locking mechanisms than those illustrated herein.

FIGS. 7-16 illustrate a grasper 310 with handle arms 318, 322, a tool body 350, and a lock 386 that locks movement of the two handle arms 318, 322 relative to one another. In some constructions the lock 386 and the handle arms 318, 322 are used in conjunction with the grasper 10 described above (e.g., in place of the handle arms 18, 22 and the lock 86, 186, or 286).

With continued reference to FIGS. 7-16, the handle arms 318, 322 are naturally biased away from one another with biasing elements 312. The illustrated biasing elements 312 are compression springs that are each coupled at one end to either the handle arm 318 or the handle arm 322, and at the other end to a central body 316 that is coupled to the tool body 350.

The grasper 310 includes ratchet arms 320, 324 that are each coupled to one of the handle arms 318, 322. The ratchet arms 320, 324 are elongate, and generally extend toward one another. In the illustrated construction the ratchet arm 320 is fixed with respect to the handle arm 318, and the ratchet arm 324 is pivotally coupled to the handle arm 322 about a pin 328. The ratchet arm 324 includes a slot 332. The ratchet arms 320, 324 each include teeth 336 (FIG. 8) that when engaged with one another hold the handle arms 318, 322 closed or otherwise prevent the handle arms 318, 322 from moving and pivoting relative to one another. The ratchet arms 320 allow a surgeon to maintain a grasp on tissue or a surgical needle without having to continuously hold the handle arms 318, 322 closed.

With continued reference to FIGS. 7-16, the grasper 310 includes a pusher element 340 with a pin 344. The illustrated pusher element 340 is disposed within the central body 316. The pin 344 is disposed within the slot 332, and is able to slide within the slot 332 as the ratchet arm 324 pivots about the pin 328. In the illustrated construction, the slot 332 is arcuate, facilitating the sliding movement of the pin 344. The grasper 310 also includes a biasing element 348 that biases the pusher element 340 (and consequently the pin 344 and the ratchet arm 324) toward the ratchet arm 320. The illustrated biasing element 348 is a compression spring disposed within the central body 316. The teeth 336 of the ratchet arms 320 and 324 engage when the handle arms 318, 322 are squeezed together because of the biasing element 348 pressing the two ratchet arms 320, 324 together.

The grasper 310 further includes a lock release element 352 coupled to (e.g., integrally formed as a single piece with) the pusher element 340. The lock release element 352 is pressed to release the ratchet arms 320, 324 (and consequently the handle arms 318, 322) from one another. The illustrated lock release element 352 is a finger grip (e.g., tab) that is pressed to slide the pusher element 340 back away from the ratchet arm 320, thereby separating the two ratchet arms 320, 324 from one another and allowing the biasing elements 312 to naturally bias the handle arms 318, 322 away from one another.

Figure 7:
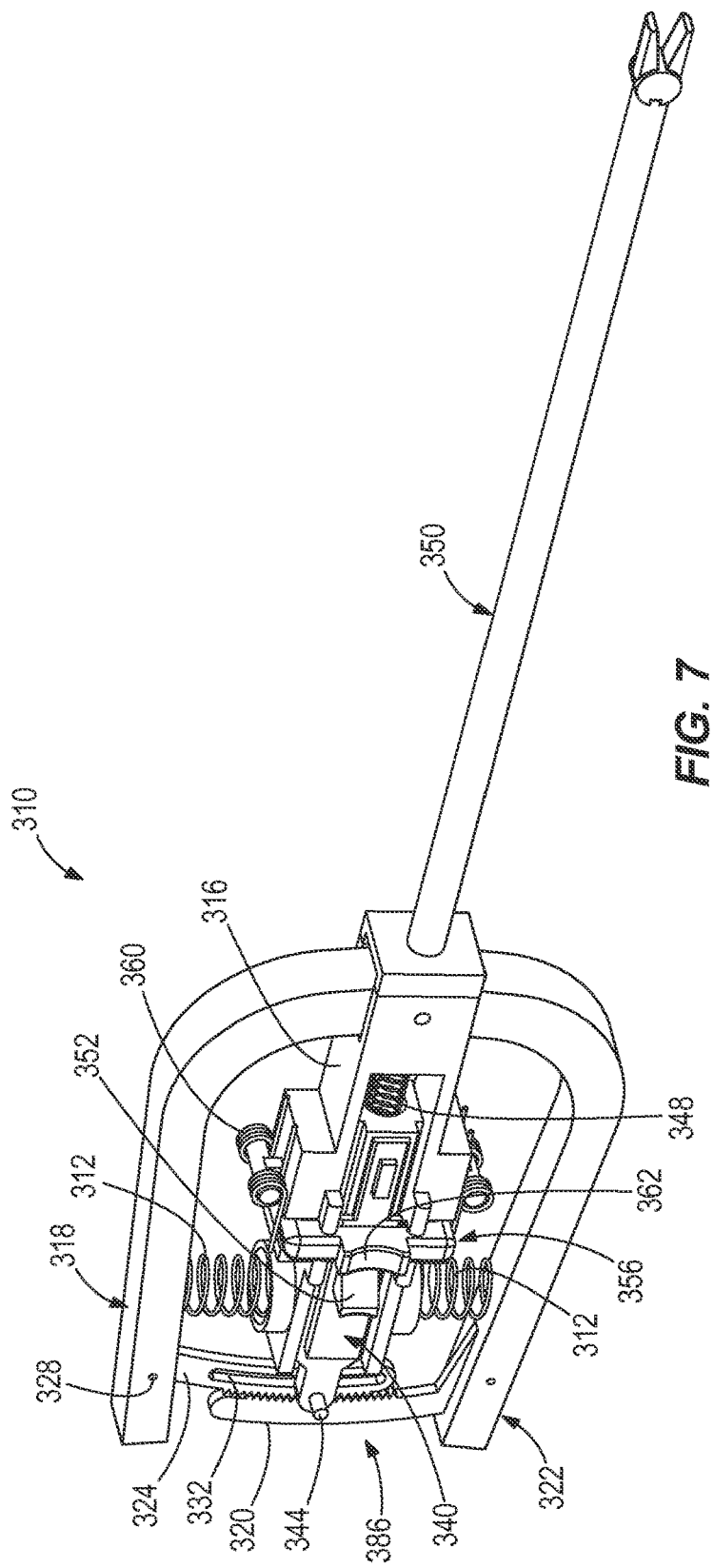
FIG. 7 is a perspective view of a grasper according to another construction of the invention.
Figure 8:
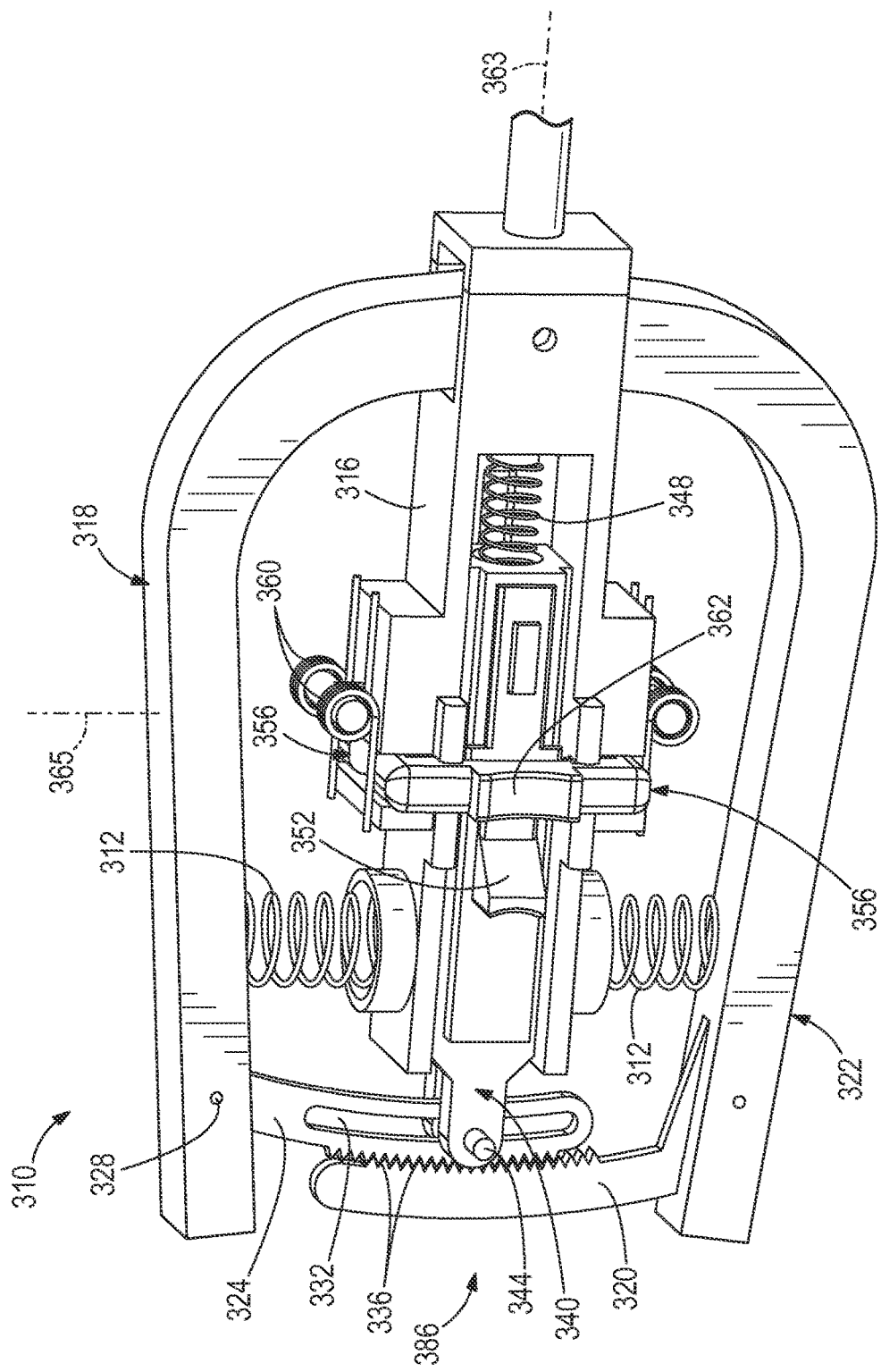
FIG. 8 is a perspective view of a portion of the grasper of FIG. 7, with ratchet arms in a normal, engaged state.
Figure 9:
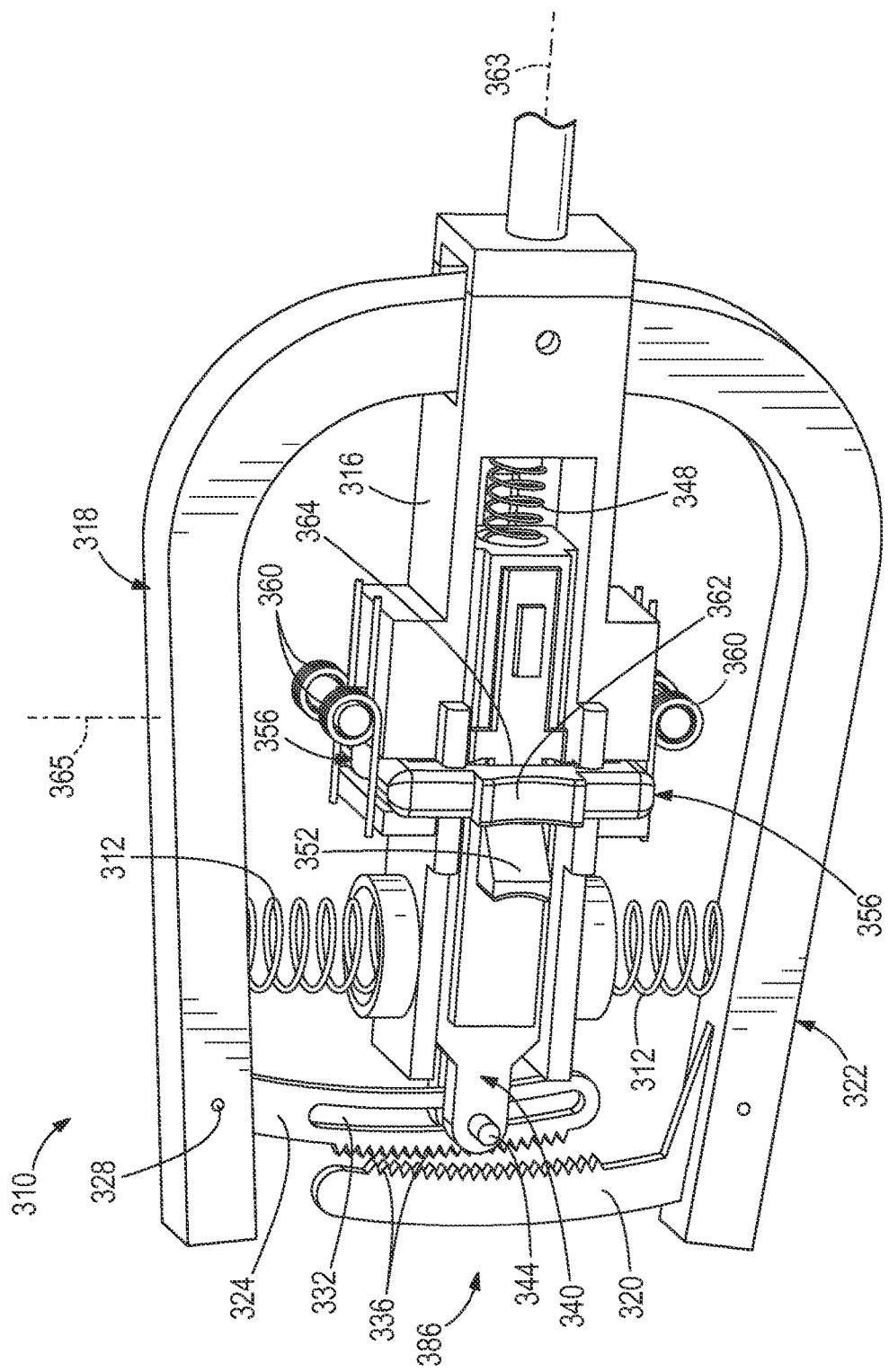
FIG. 9 is a perspective view of a portion of the grasper of FIG. 7, with the ratchet arms in a disengaged state, and a pusher element pressed back.

The grasper 310 further includes at least one lockout element 356 and a biasing element or elements 360 that bias the lockout element 356 toward a centered, neutral position (as seen, for example, in FIGS. 7-9). The illustrated construction includes two independent lockout elements 356, one on either side of the grasper 310 (e.g., to provide comfort and ease of use for a right-handed surgeon and a left-handed surgeon), although other constructions include different numbers of lockout element 356. Each lockout element 356 is used to lock a position of the pusher element 340 when the pusher element 340 has been pressed back and away from the ratchet arm 320. Each lockout element 356 prevents the teeth 336 of the ratchet arms 320, 324 from engaging. Each lockout element 356 includes finger grips 362 for easily gripping and moving the lockout element 356.

Operation of the grasper 310 is illustrated with reference to FIGS. 8-16.

With reference to FIG. 8, the grasper 310 is in a normal operating state, where the ratchet arms 320, 324 are engaged with one another, the pusher element 340 is biased fully toward the ratchet arm 320, and the lockout element 356 is in its centered, neutral position.

With reference to FIG. 9, the lock release element 352 is then pressed back against the force of the biasing element 348 along an axis 363 to disengage the ratchet arms 320, 324, causing the pusher element 340 to slide back and the ratchet arm 324 to pull away from the ratchet arm 320. As the pusher element 340 slides back, a portion of the pusher element 340 slides through an opening 364 in the lockout element 356.

Figure 10:
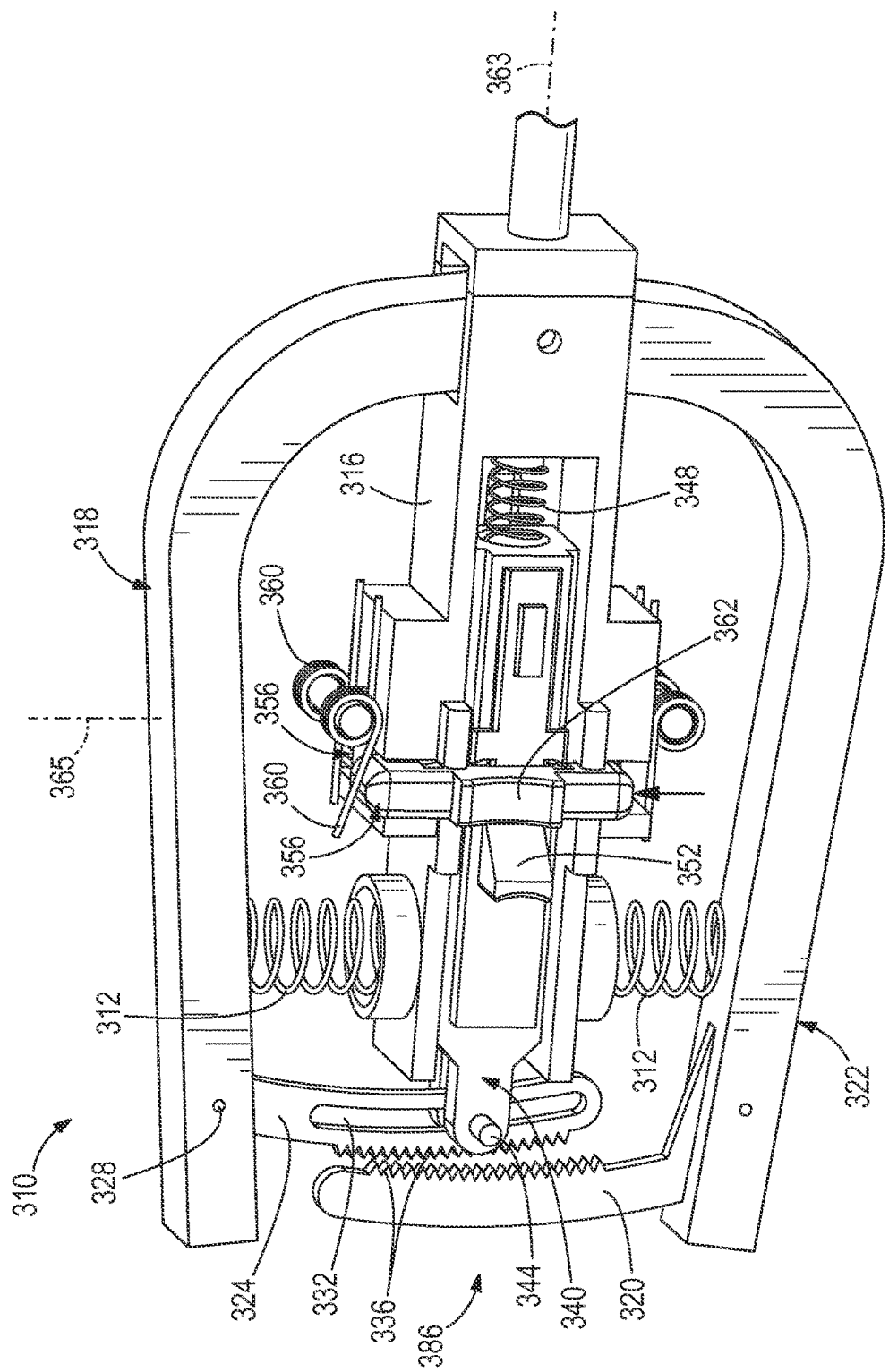
FIGS. 10-12 are perspective views of a portion of the grasper of FIG. 7, with a lockout element pressed up and engaged with the pusher element.
Figure 11:
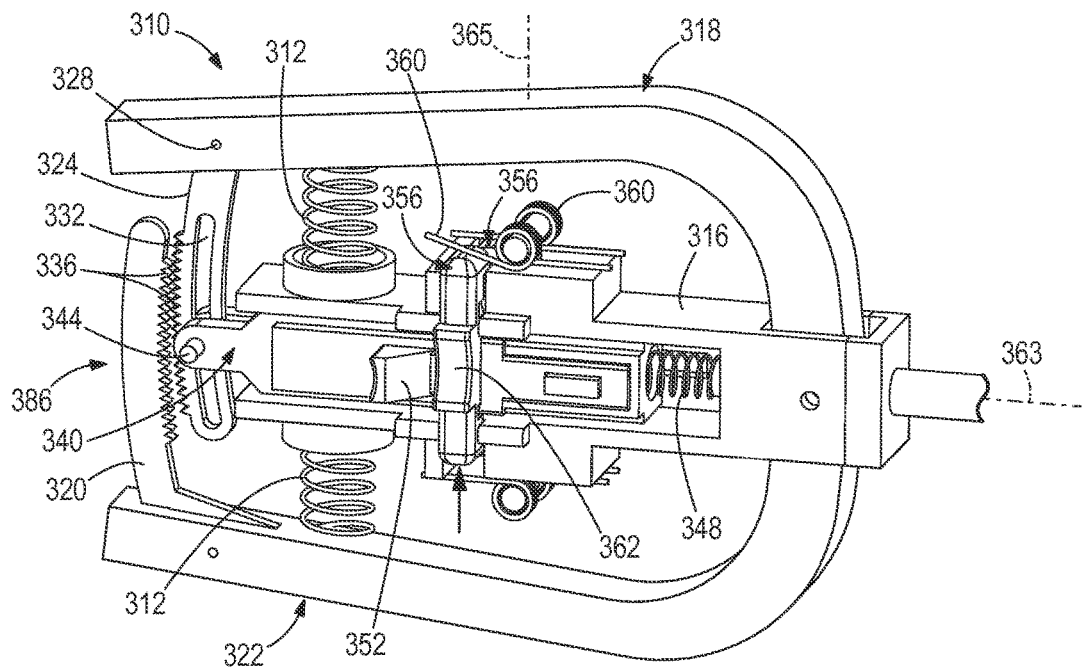

With reference to FIGS. 10 and 11, one of the lockout elements 356 is then pressed up along an axis 365 against the force of the biasing element 360, with the pusher element 340 still being held back against the force of the biasing element 348. In the illustrated construction, the axis 365 is perpendicular to the axis 363.

Figure 12:
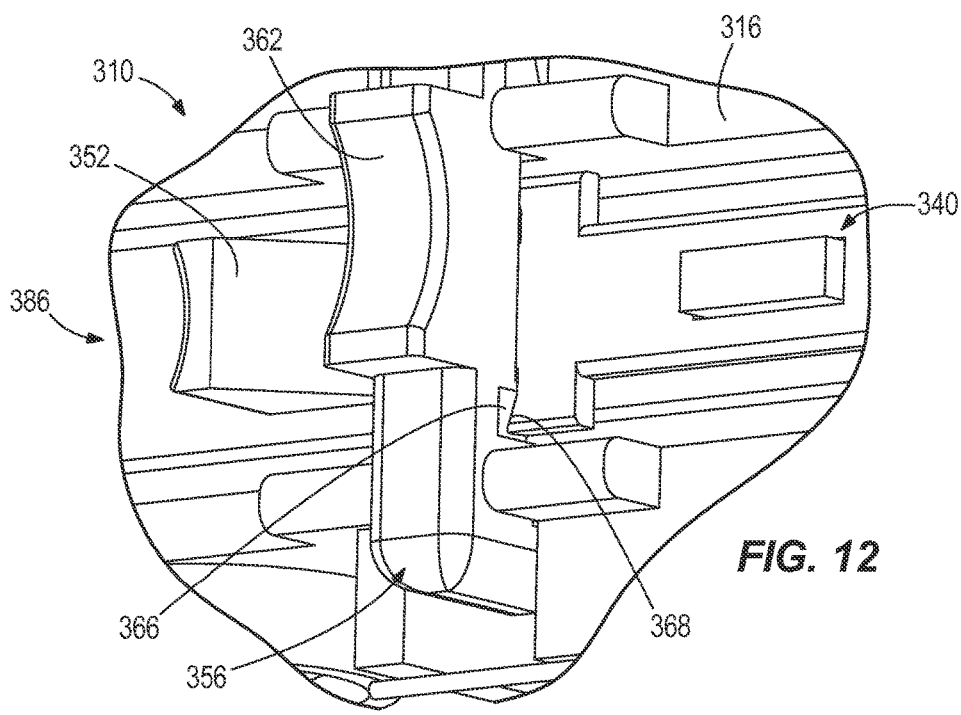
Figure 17:
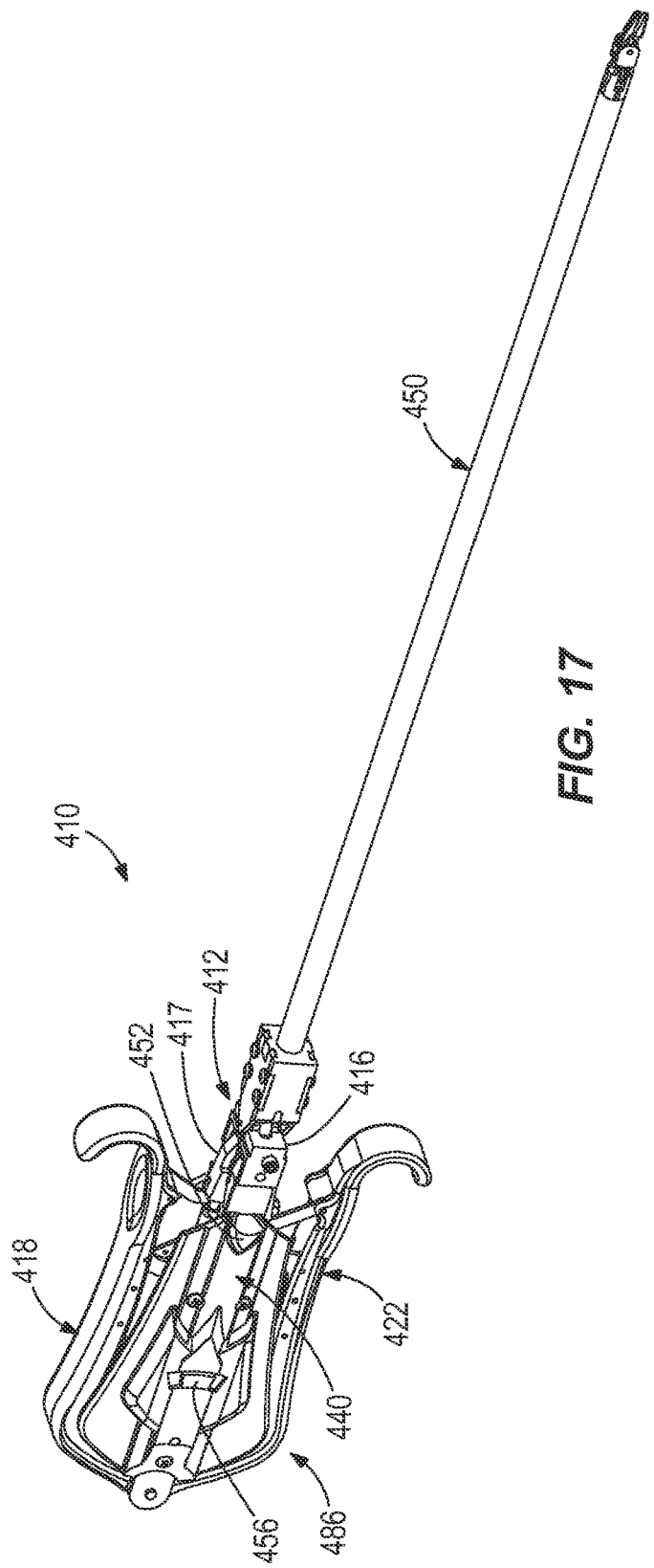
FIG. 17 is a perspective view of a grasper according to another construction of the invention.

With reference to FIG. 12, each lockout element 356 includes a mating component 366, and the pusher element 340 includes a mating component 368. The mating components 366, 368 are aligned to engage with one another when the lockout element 356 has been pressed up far enough against the force of the biasing element 360 into a mating position. In the illustrated construction the mating component 366 is a recess and the mating component 368 is a projection. Other constructions include different structures.

With continued reference to FIG. 12, once the mating components 366, 368 are aligned, the pusher element 340 is released (e.g., by the surgeon releasing his or her grip on the lock release element 352). The biasing element 348 then naturally biases and presses the mating component 368 into the mating component 366. With the mating components 366, 368 engaged, the surgeon can then release the finger grip or grips 362 on the lockout element 356, and the lockout element 356 will remain fixed (as illustrated in FIG. 13) away from the centered position. In this position the pusher element 340 is locked and unable to move back toward the ratchet arm 320 along the axis 363. In some constructions the mating components 366, 368 are merely friction surfaces that engage and hold the lockout element 356 in place when the pusher element 340 is released. Other constructions include different structures for the mating components 366, 368.

With reference to FIGS. 13-16, to release the lockout element 356 the lock release element 352 is again pressed against the force of the biasing element 348, thereby disengaging the mating component 368 from the mating component 366. As illustrated in FIGS. 14 and 15, with the mating components 366, 368 disengaged the lockout element 356 naturally returns to its centered position due to the force of the biasing element 360 pressing the lockout element 356 down (toward the axis 363) along the axis 365. As illustrated in FIG. 16, the lock release element 352 is then released by the surgeon and the ratchet arms 320, 324 again engage one another due to the force of the biasing element 348.

The illustrated grasper 310 is symmetrical about the central body 316, such that control is identical both left to right as well as when the grasper 310 is rolled 180 degrees about an axis defined by the tool body 350. The grasper 310 includes lock release elements 352 on both sides of the grasper 310, as well as finger grips 362 for the lockout elements 356 on both sides of the grasper 310, so that a surgeon may control the grasper 310 on either side of the grasper 310.

FIGS. 17-20 illustrate a grasper 410 similar to the grasper 310, with handle arms 418, 422, a tool body 450, and a lock 486 including a pusher element 440, a lock release element 452, and a lockout element 456. In some constructions the lock 486 and the handle arms 418, 422 may be used in conjunction with the grasper 10 or 310 described above (e.g., in place of the handle arms 18, 22, 318, 322 and one of the locking mechanisms 86, 186, 286, or 386).

Figure 18:
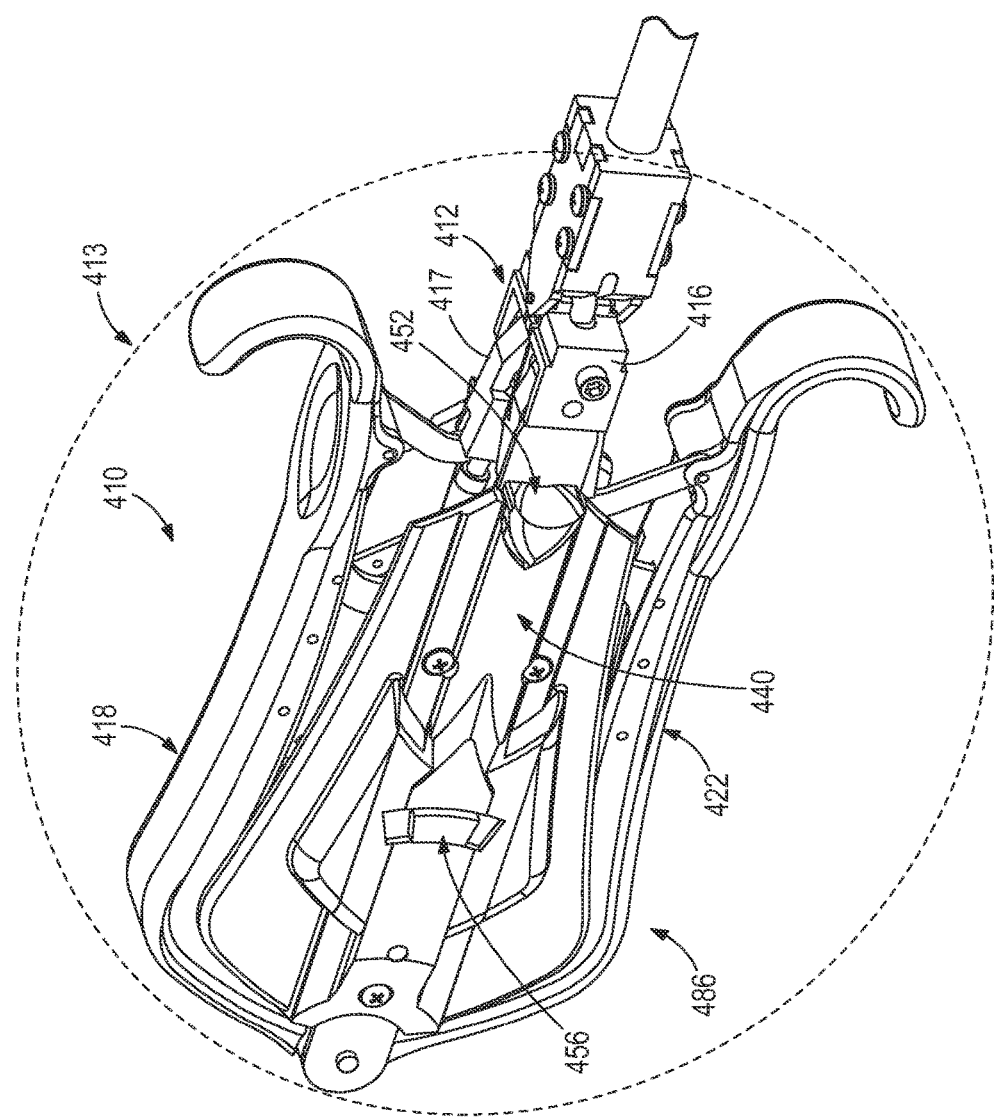
FIGS. 18-20 are perspective views of a portion of the grasper of FIG. 17.

The grasper 410 is a dexterous grasper having a pivot block 412 that permits the handle arms 418, 422 (and the surgeon's wrist) to twist in multiple degrees of freedom relative to the tool body 450. The pivot block 412 is a wrist joint that is substantially or entirely disposed within a grip volume 413 (FIG. 18). The grip volume 413 is defined as an area that generally corresponds to where a surgeon grips the grasper 410, that encompasses the two handle arms 418, 422, and that is separate from the tool body 450. In some constructions the handle arms 18, 22, 318, 322, along with the lock 86, 186, 286, 386 of FIGS. 1-16, are also all disposed within a grip volume similar to that of grip volume 413 (i.e., are disposed in an area where a surgeon grips the grasper 10, 310, and that is separate from the tool body 50, 350).

Figure 19:
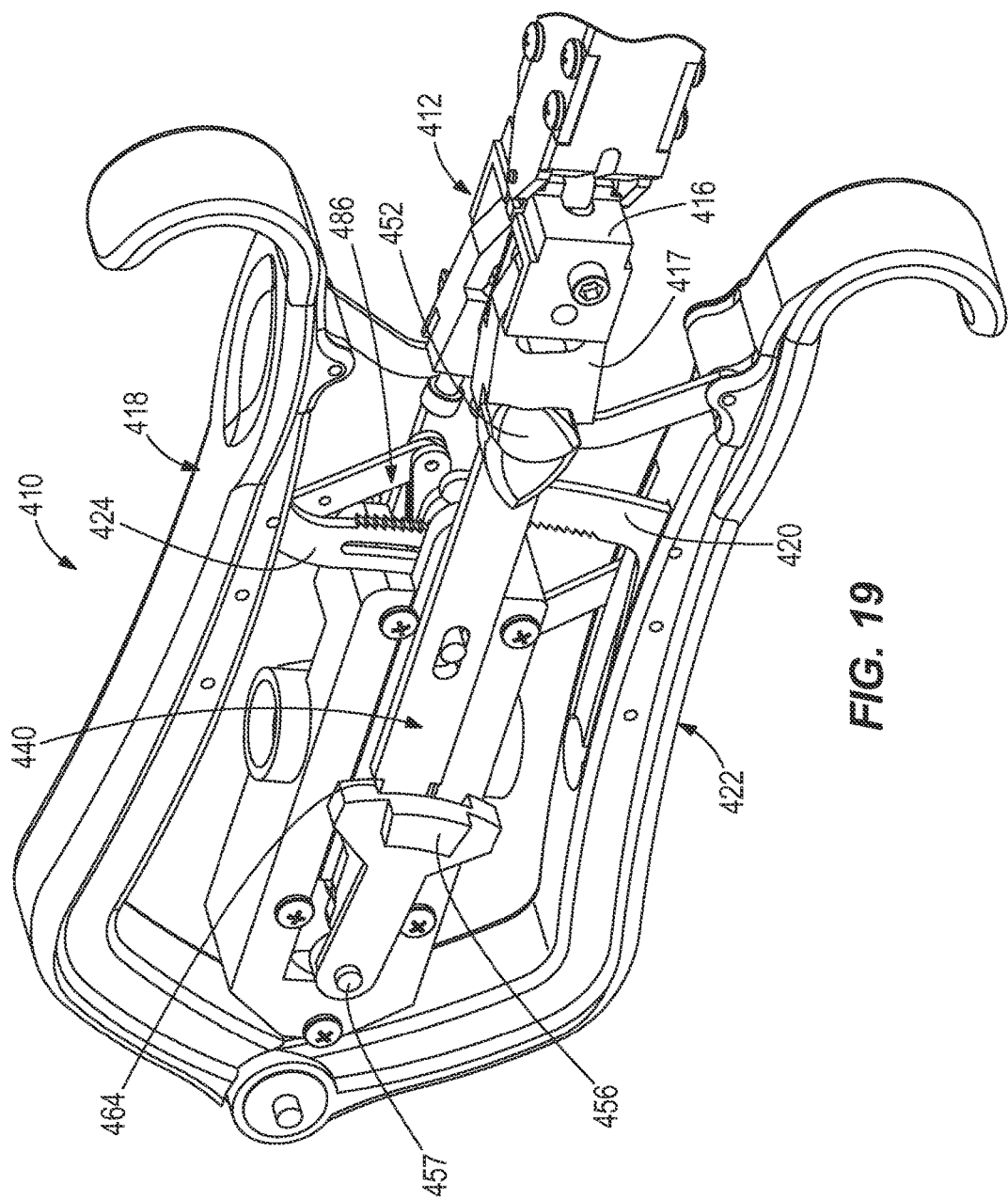
Figure 20:
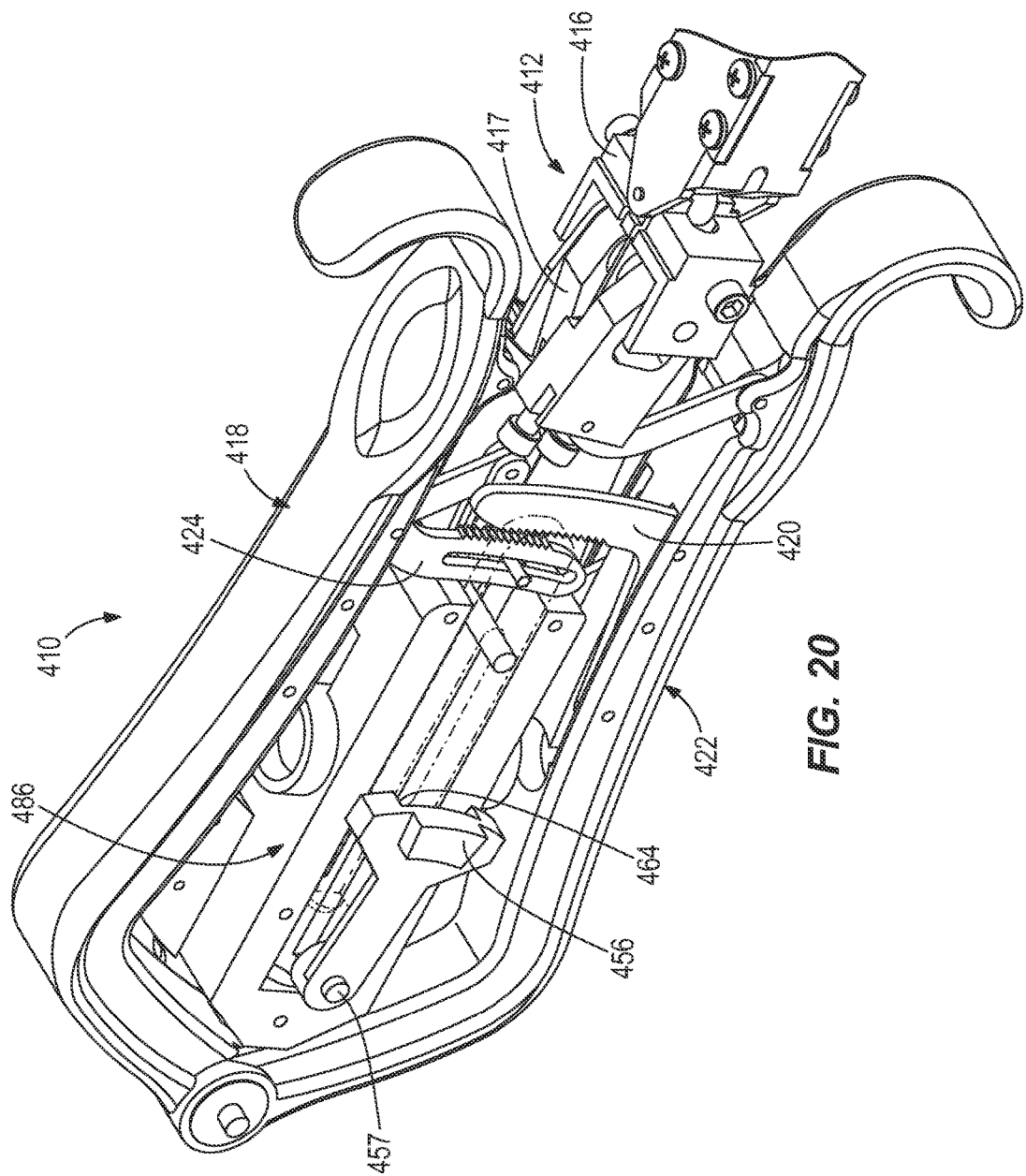

In the illustrated construction the handle arms 418, 422 each extend to at least some degree over the pivot block 412. With reference to FIGS. 18-20, the pivot block 412 includes a first pivotable member 416 that is coupled to the tool body 450 and pivots laterally (e.g., left and right) relative to the tool body 450, and a second pivotable member 417 coupled to the first pivotable member 416 and to the handle arms 418, 422 that pivots in a transverse direction (e.g., up and down) relative to the first pivotable member 416. In some constructions the pivot block 412, or another similar structure, may be used in conjunction with the grasper 10 or 310 described above, to permit multiple degrees of freedom of the handle arms 18, 22, 318, 322 relative to the tool body 50, 350. In some constructions one or more of the degrees of freedom may be temporarily locked, so that only a single degree of freedom is provided.

With continued reference to FIGS. 18-20, the grasper lock 486 is similar to the lock 386 of grasper 310, and includes ratchet arms 420, 424 and a lock release element 452. In some constructions the ratchet arm 420 is fixed, and the ratchet arm 424 is pivotable relative to the handle arm 418. When the lock release element 452 is pressed back (e.g., against the force of a spring), the lockout element 456 pivots about a pivot point 457 (FIGS. 19 and 20), such as a pivot pin, or is otherwise moved. With continued reference to FIGS. 19 and 20, in the illustrated construction the pusher element 440 slides within an opening 464 in the lockout element 456, similar to the openings 364. When the lockout element 456 is moved (e.g., pivoted), the lockout element 456 engages the pusher element 440 (e.g., with mating components like mating components 366, 368) so as to hold or lock the pusher element 440 in place and keep the ratchet arms 420, 424 apart. In contrast to the handle arms 318, 322 and the ratchet arms 320, 324, the handle arms 418, 422 and the ratchet arms 420, 424 of the grasper 410 are more ergonomically designed and are disposed closer to the tool body 450, to provide for greater ease and comfort during use of the grasper 410. For example, as illustrated in FIG. 18, both the handles arms 418, 422 as well as the grasper lock 486 are disposed within the grip volume 413.

While the handle arms 18, 22, 318, 322, 418, 422, tool bodies 50, 350, 450, jaws 62, 64, and ratchet arms 324, 424 described above are described as being pivotally coupled to one or more other components with pulleys and/or pins, other structures may also or alternatively be used to pivotally couple these components to other components within the graspers 10, 310, 410. For example, in some constructions flexural hinges may be used in place of or in addition to the pulleys and/or pins.

Although the invention has been described in detail with reference to certain preferred embodiments, variations and modifications exist within the scope and spirit of one or more independent aspects of the invention as described.

The invention claimed is:

1. A surgical grasper comprising:
a first handle arm;
a second handle arm coupled to the first handle arm; and
a lock that locks relative movement between the first and second handle arms, the lock including:
a first ratchet arm fixed to the first handle arm;
a second ratchet arm coupled to the second handle arm;
a pusher element slidably coupled to the second ratchet arm that moves the second ratchet arm toward and away from the first ratchet arm; and
a lockout element releasably coupled to the pusher element that locks a position of the pusher element.

2. The surgical grasper of claim 1, further comprising a first biasing element coupled to the first handle arm that biases the first handle arm away from the second handle arm, and a second biasing element coupled to the second handle arm that biases the second handle arm away from the first handle arm.

3. The surgical grasper of claim 2, further comprising a third biasing element (348) that biases the pusher element.

4. The surgical grasper of claim 1, wherein the second ratchet arm includes a slot, and wherein the pusher element includes a pin that slides within the slot.

5. The surgical grasper of claim 1, wherein the pusher element includes a lock release element, wherein the lock release element is a finger grip that when pressed causes the pusher element to move the second ratchet arm away from the first ratchet arm.

6. The surgical grasper of claim 1, wherein the lock includes a biasing element that biases the pusher element toward the first ratchet arm.

7. The surgical grasper of claim 1, wherein the lockout element includes a finger grip that when pressed causes the lockout element to move relative to the pusher element.

8. The surgical grasper of claim 1, wherein the lockout element includes a first mating component and the pusher element includes a second mating component configured to mate with the first mating component when the lockout element is in a mating position with the pusher element.

9. The surgical grasper of claim 8, wherein the lock includes a biasing element that biases the lockout element away from the mating position.

10. The surgical grasper of claim 1, wherein the pusher element is movable along a first axis and the lockout element is movable along a second axis, and wherein the first axis is perpendicular to the second axis.

11. The surgical grasper of claim 1, wherein the lockout element is a first lockout element, and wherein the lock includes a second lockout element releasably coupled to the pusher element.

12. The surgical grasper of claim 1, further comprising a tool body coupled to both the first handle arm and second handle arm, wherein the tool body is an elongated body extending along a longitudinal direction, and wherein the pusher element is configured to slide along the longitudinal direction.

13. The surgical grasper of claim 1, wherein the first handle arm includes a free distal end extending toward the first jaw member and the second handle arm includes a free distal end extending toward the second jaw member.

14. A surgical grasper comprising:
a first handle arm;
a second handle arm coupled to the first handle arm;
a first biasing element coupled to the first handle arm that biases the first handle arm away from the second handle arm;
a second biasing element coupled to the second handle arm that biases the second handle arm away from the first handle arm; and
a lock that locks relative movement between the first and second handle arms, the lock including:
 a first ratchet arm fixed to the first handle arm;
 a second ratchet arm coupled to the second handle arm;
 a pusher element coupled to the second ratchet arm that moves the second ratchet arm toward and away from the first ratchet arm; and
 a lockout element releasably coupled to the pusher element that locks a position of the pusher element.

15. The surgical grasper of claim 14, further comprising a third biasing element (348) that biases the pusher element.

16. The surgical grasper of claim 14, further comprising a tool body coupled to both the first handle arm and second handle arm, wherein the tool body is an elongated body extending along a longitudinal direction, and wherein the pusher element is configured to slide along the longitudinal direction.

17. A surgical grasper comprising:
a first handle arm;
a second handle arm coupled to the first handle arm; and
a lock that locks relative movement between the first and second handle arms, the lock including:
 a first ratchet arm fixed to the first handle arm;
 a second ratchet arm coupled to the second handle arm;
 a pusher element coupled to the second ratchet arm that moves the second ratchet arm toward and away from the first ratchet arm;
 a lockout element releasably coupled to the pusher element that locks a position of the pusher element, wherein the lockout element includes a first mating component and the pusher element includes a second mating component configured to mate with the first mating component when the lockout element is in a mating position with the pusher element, and
 a biasing element that biases the lockout element away from the mating position.

18. The surgical grasper of claim 17, further comprising a tool body coupled to both the first handle arm and second handle arm, wherein the tool body is an elongated body extending along a longitudinal direction, and wherein the pusher element is configured to slide along the longitudinal direction.

19. A surgical grasper comprising:
a first handle arm;
a second handle arm coupled to the first handle arm; and
a lock that locks relative movement between the first and second handle arms, the lock including:
 a first ratchet arm fixed to the first handle arm;
 a second ratchet arm coupled to the second handle arm;
 a pusher element coupled to the second ratchet arm that moves the second ratchet arm toward and away from the first ratchet arm; and
 a lockout element releasably coupled to the pusher element that locks a position of the pusher element;
 wherein the pusher element is movable along a first axis and the lockout element is movable along a second axis, and wherein the first axis is perpendicular to the second axis.

20. A surgical grasper comprising:
a first handle arm;
a second handle arm coupled to the first handle arm; and
a lock that locks relative movement between the first and second handle arms, the lock including:
 a first ratchet arm fixed to the first handle arm;
 a second ratchet arm coupled to the second handle arm;
 a pusher element coupled to the second ratchet arm that moves the second ratchet arm toward and away from the first ratchet arm;
 a first lockout element releasably coupled to the pusher element that locks a position of the pusher element; and
 a second lockout element releasably coupled to the pusher element.

* * * * *